United States Patent
Yamagata (10) Patent No.: US 8,024,085 B2
(45) Date of Patent: Sep. 20, 2011

(54) DRIVING SUPPORT SYSTEM

(75) Inventor: Toshihiro Yamagata, Ama-gun (JP)

(73) Assignee: DENSO CORPORATION, Kariya (JP)

( * ) Notice: Subject to any disclaimer, the term of this patent is extended or adjusted under 35 U.S.C. 154(b) by 401 days.

(21) Appl. No.: 12/379,708

(22) Filed: Feb. 26, 2009

(65) Prior Publication Data
US 2009/0216396 A1   Aug. 27, 2009

(30) Foreign Application Priority Data

Feb. 27, 2008   (JP) .................... 2008-046117

(51) Int. Cl.
B60L 3/00   (2006.01)
(52) U.S. Cl. ............ 701/33; 701/22; 340/439; 340/576; 180/272
(58) Field of Classification Search ............ 701/22, 701/29, 33, 123; 340/439, 576; 180/271, 180/272
See application file for complete search history.

(56) References Cited

U.S. PATENT DOCUMENTS

| 5,942,979 | A * | 8/1999 | Luppino ............ 340/576 |
| 7,187,292 | B2 * | 3/2007 | Hayashi et al. ............ 340/576 |
| 7,751,954 | B2 * | 7/2010 | Matsuda et al. ............ 701/31 |
| 2008/0105482 | A1 | 5/2008 | Yamaguchi et al. |

FOREIGN PATENT DOCUMENTS

| JP | A-2001-256036 | 9/2001 |
| JP | A-2003-023378 | 1/2003 |
| JP | A-2003-023442 | 1/2003 |
| JP | A-2006-103393 | 4/2006 |
| JP | A-2007-057510 | 3/2007 |
| JP | A-2008-061931 | 3/2008 |
| JP | A-2008-113946 | 5/2008 |

* cited by examiner

Primary Examiner — Paul N Dickson
Assistant Examiner — Timothy Wilhelm
(74) Attorney, Agent, or Firm — Posz Law Group, PLC

(57) ABSTRACT

The navigation apparatus in a vehicle receives physical condition data regarding user's condition from a measurement instrument through a power line when the vehicle is connected to the power line. The navigation apparatus determines whether a travel condition of the vehicle that is driven by using the sensors disposed in the vehicle, in terms of the driving operation concerning the fuel consumption rate of the vehicle. If the driving operation is not determined as fuel-consumption-conscious, an advice for the driving operation is output from the navigation apparatus according to the physical condition of the user. The user thus can have an appropriate advice for the driving operation that improves the fuel consumption rate of the vehicle at an appropriate timing that takes into consideration of the physical condition of the user under measurement outside of the vehicle.

5 Claims, 8 Drawing Sheets

| BODY TEMP<br>NORMALITY RANGE:<br>MAX 36.7°C<br>MIN 35.2°C | BLOOD PRESSURE<br>NORMALITY RANGE:<br>MAX 130 OR UNDER<br>MIN 90 OR UNDER | PULSE INTERVAL<br>NORMALITY RANGE:<br>MAX 1.2s<br>MIN 0.7s | DETERMINATION RESULT |
|---|---|---|---|
| WITHIN RANGE | WITHIN RANGE | WITHIN RANGE | GOOD |
| | | OUT OF RANGE | NORMAL |
| | OUT OF RANGE | WITHIN RANGE | NORMAL |
| | | OUT OF RANGE | BAD |
| OUT OF RANGE | WITHIN RANGE | WITHIN RANGE | NORMAL |
| | | OUT OF RANGE | BAD |
| | OUT OF RANGE | WITHIN RANGE | BAD |
| | | OUT OF RANGE | BAD |

DRIVING SUPPORT SYSTEM

CROSS REFERENCE TO RELATED APPLICATION

The present application is based on and claims the benefit of priority of Japanese Patent Applications No. 2008-46117, filed on Feb. 27, 2008, the disclosure of which is incorporated herein by reference.

FIELD OF THE DISCLOSURE

The present disclosure generally relates to a driving support system that utilizes a power line communication.

BACKGROUND INFORMATION

In recent years, a driving support system that uses sensors and/or equipments in a vehicle for collecting a travel condition data of the vehicle and outputs an advice for driving operation for a user based on the collected data is proposed, for example, in Japanese patent document JP-A-2001-256036 (e.g., paragraphs [0025], [0052] etc.)

Also, in recent years, electric vehicles and hybrid vehicles connected to an outlet at home by using a plug for charging the battery are considered as a subject of research and development. While the battery in the vehicle is charged by the electricity provided through the power line, a device outside of the vehicle and a vehicular equipment is connected through a power line communication for data exchange, in a technique disclosed, for example, Japanese patent documents JP-A-2003-23378, and JP-A-2003-23442.

In the technique in the above document (JP-A-2001-256036), the vehicle's travel condition collected by the equipment is used to determine/notify a degree of safeness of the travel condition, and to provide an advice for improving the safety of the travel condition.

Therefore, the user may be able to improve the fuel consumption rate if he/she takes the provided advice and reflects the advice to the driving operation for decreasing the frequency of the abrupt acceleration/deceleration/braking. Further, if the fuel consumption rate is improved, that leads to a favorable condition for the environmental issues such as a global warming due to the reduction of the carbon dioxide exhausted as the exhaust gas from the vehicle.

However, if the advice for the driving operation is provided too frequently, the user may feel it uncomfortable. On the other hand, the frequently-provided advice may be beneficial if the user is, for example, in a physically bad condition and is having a deteriorated condition in terms of attentiveness.

Therefore, in the technique in the above document (JP-A-2001-256036), providing the advice at an appropriate timing was the problem. In particular, the appropriate determination whether the user is having a bad physical condition or a good one was difficult because the appropriate determination should be based on the examination performed at a time when the user is resting. That is, in other words, the user in the vehicle is not resting, thereby making it difficult for appropriately determining the physical condition of the user in an accurate manner.

SUMMARY OF THE DISCLOSURE

In view of the above and other problems, the present disclosure provides a driving support system that considers the physical condition of the user, based on the data taken at an outside of the vehicle, for appropriately providing the advice concerning the driving operation, as well as improving the fuel consumption rate and contributing to the environmental problems.

In an aspect of the present disclosure, the driving support system for supporting a user who is driving a vehicle includes: a physical condition measuring unit for measuring a physical condition of the user and for generating a condition data at an outside of a vehicle; and an information processor disposed on the vehicle for (a) receiving the condition data from the physical condition measuring unit through a power line that connects a battery in the vehicle and a power supply unit outside the vehicle for charging the battery, and for (b) providing an advice for driving operation at a timing that takes into consideration the physical condition of the user estimated from the condition data after (c) examining if the user is performing a fuel-consumption-conscious driving operation and (d) determining that the user is not performing the fuel-consumption-conscious driving operation (e) based on a vehicle condition reflecting driving operation of the user derived from sensors in the vehicle when the user is driving the vehicle.

By devising the above scheme, while the user is at an outside of the vehicle, the physical condition data for determining the user's condition is collected and transferred to the vehicle. Therefore, when the user is driving the vehicle, an appropriate advice for improving the fuel consumption rate in terms of the driving operation is provide for the user based on the condition data collected in advance at an outside of the vehicle. Further, if the driver takes the advice provided at an appropriate timing, the fuel consumption rate is improved, thereby leading to the contribution to the environmental problems.

BRIEF DESCRIPTION OF THE DRAWINGS

Objects, features, and advantages of the present disclosure will become more apparent from the following detailed description made with reference to the accompanying drawings, in which.

DETAILED DESCRIPTION

Next, the embodiments of the present invention are described by using the concrete examples.

(Explanation of Configuration of Driving Support System)

Figure 1A:
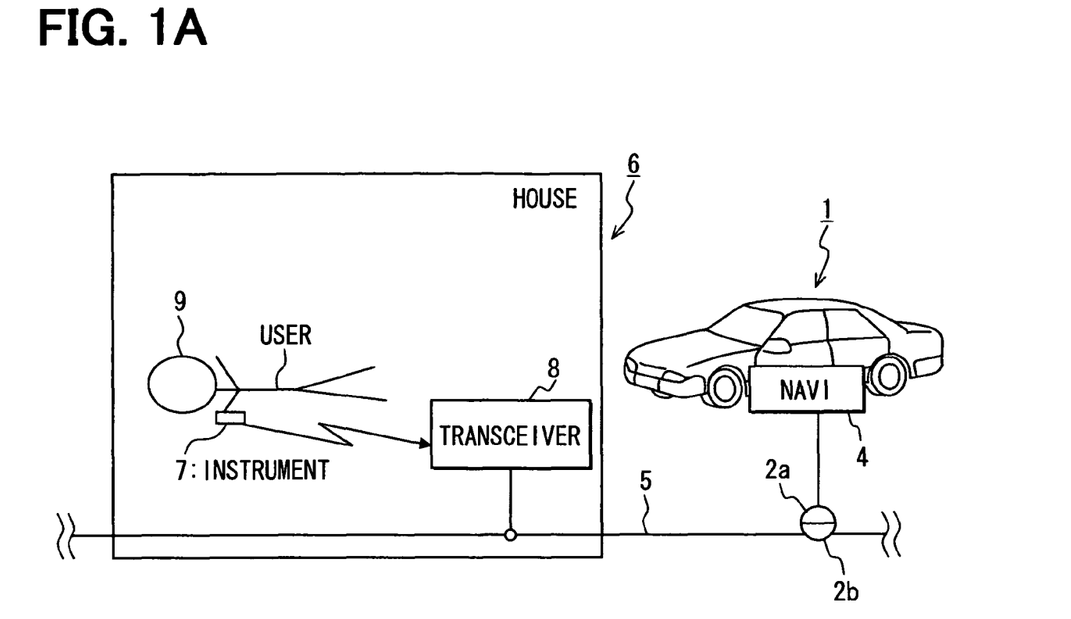
FIGS. 1A and 1B are illustrations of a driving support system and an instrument for measuring a physical condition of a user.

FIG. 1A is an outline illustration of the driving support system in the embodiment of the present invention. The driving support system described as follows has following components. That is, a vehicle navigation apparatus 4 disposed in a vehicle 1, a physical condition measurement instrument 7 in a user's house 6, a transceiver 8 for serving as a data transmission route between the navigation apparatus 4 and the instrument 7, an electric power line 5, and the like.

Figure 1B:
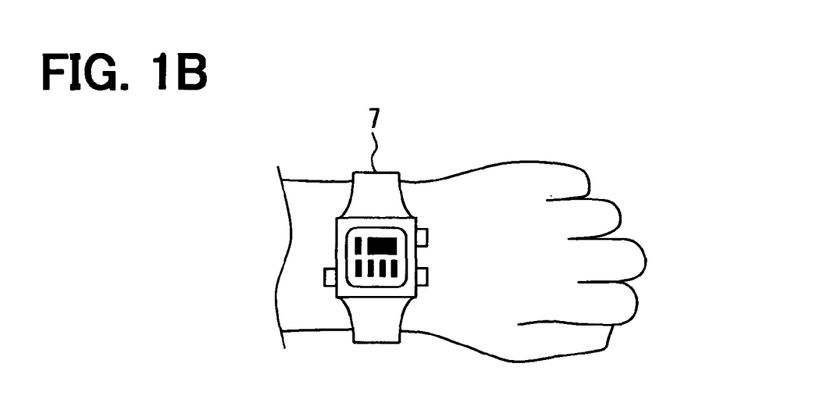

The physical condition measurement instrument 7 is a wrist watch type instrument that measures the body temperature, the blood pressure, and the pulse interval of a user 9 while the user 9 is sleeping, and the measurement results are stored as data in an internal memory as shown in FIG. 1B.

In details, the physical condition measurement instrument 7 determines whether the user 9 is sleeping based on the pulse interval, the body temperature and the like, and, when it is determined that the user 9 is sleeping, measures the physical condition of the user 9 for every 1.5 hours to store the physical condition data in the internal memory.

In the present embodiment, the elements measured as physical condition data are the body temperature, the blood pressure, and the pulse interval. As the body temperature, the mean value of one minute measurement is taken as the condition data. Likewise, the highest/lowest pressures are taken as the blood pressure of the condition data as well as the longest/shortest intervals of the pulse interval are taken as the condition data.

While the electric power line communication is performed between the navigation apparatus 4 and the transceiver 8, the transceiver 8 communicates with the instrument 7 through the wireless connection. The transceiver 8 thus relays, as a network device, the data exchanged between the navigation apparatus 4 and the instrument 7.

The vehicle 1 has the navigation apparatus 4 and a battery having a plug 2a not shown in the figure. Further, when the plug 2a is inserted into an outlet 2b on the power line 5, the battery is charged by the electricity provided from outside of the vehicle through the electric power line 5. Furthermore, when the plug 2a is inserted into the outlet 2b, the navigation apparatus 4 is put in a power line communication enabled condition through the electric power line 5 with the devices outside of the vehicle. Therefore, the physical condition data sent from the measurement instrument 7 in the user's house 6 by way of the transceiver 8 in such a state.

Figure 2:
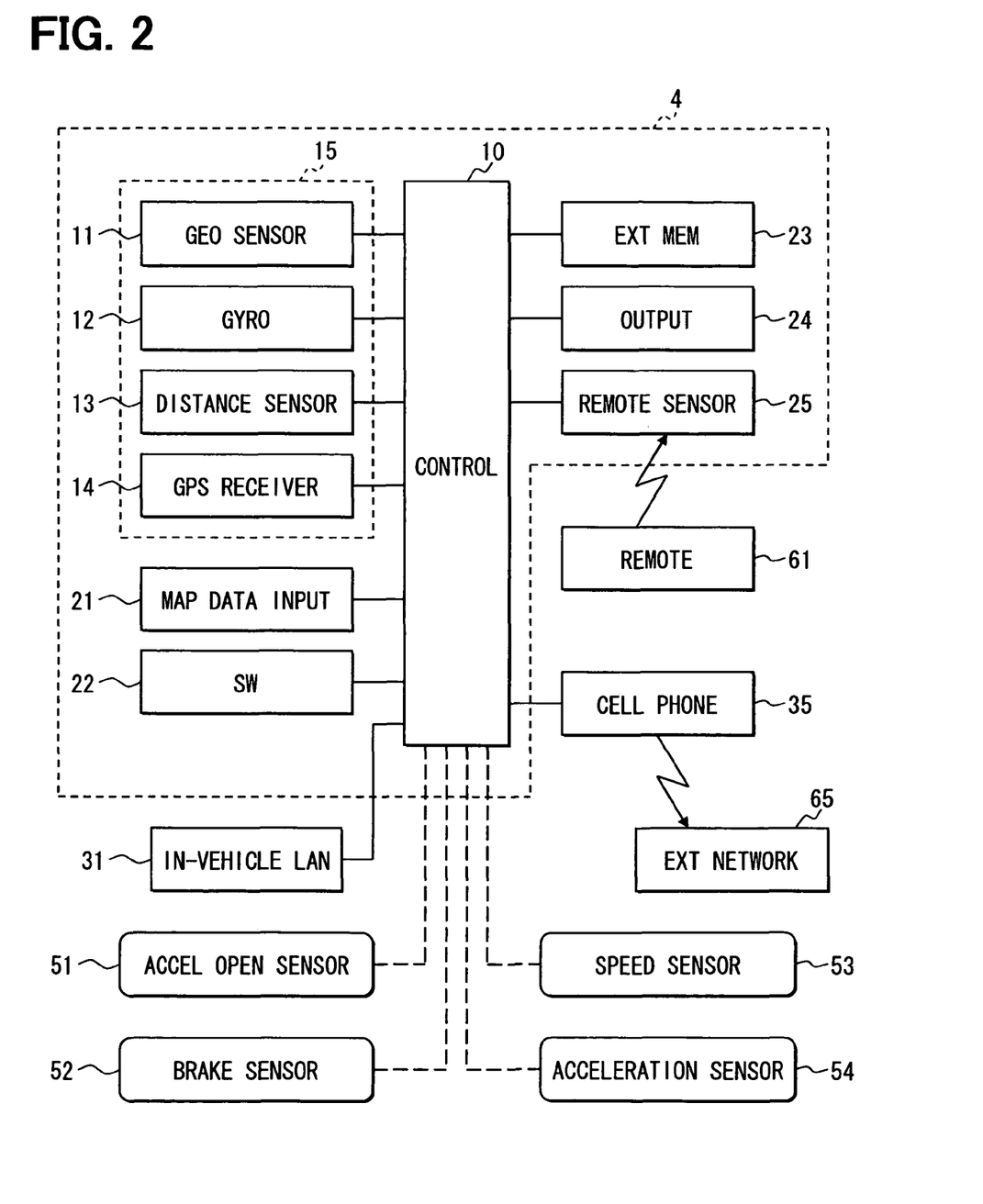
FIG. 2 is a outline block diagram of a navigation apparatus used in a vehicle in an embodiment of the present disclosure.

Next, FIG. 2 is an outline block diagram of an in-vehicle equipment of vehicle 1. In this case, only the in-vehicle equipment used in the embodiment of the driving support system of the present invention is shown in FIG. 2 though various in-vehicle equipments are installed in the vehicle.

The vehicle 1 has an in-vehicle LAN 31 together with the navigation apparatus 4. The navigation apparatus 4 has a control unit 10, a position detector 15, a map data input unit 21, an operation switch group 22, an external memory 23, an output unit 24, and a remote control sensor 25.

The control unit 10 is composed as a well-known microcomputer having a CPU, a ROM, a RAM, an I/O, and a bus line for interconnection of these parts. The control unit 10 executes various processing based on programs stored in the ROM and RAM.

The position detector 15 detects a present location of the vehicle by using a geo magnetism sensor 11, a gyroscope 12, a distance sensor 13, and the GPS receiver 14. The geo magnetism sensor 11 detects the travel direction of the vehicle from terrestrial magnetism. The gyroscope 12 detects the size of rotation applied to the vehicle. The distance sensor 13 detects the travel distance based on a back and forth acceleration of the vehicle with other clues. The GPS receiver 14 receives, through a GPS antenna (not shown) the electric wave from the space satellite of the Global Positioning System (GPS). The equipments 11 to 14 in the above-mentioned position detector 15 is connected to the control unit 10 having the detection results and the like of each equipment ready to be output to the control unit 10.

The map data input unit 21 is a device to input various data memorized in the map storage medium not shown in the figure from the map storage medium, and the input unit 21 is connected with the control unit 10 in a condition that allows various inputted data to be output to the control unit 10. The map data storage medium stores various data such as the map data (node data, link data, cost data, road data, geographical features data, mark data, intersection data, and facilities data, etc.), the guidance voice data, the voice recognition data, and the like. The storage medium type includes a CD-ROM, a DVD-ROM, a hard disk drive, a memory card, and the like.

The operation switch group 22 is used to input various instructions from the user, and the switch group 22 is connected with the control unit 10 in a condition that allows signals according to the inputted instructions to be output to the control unit 10. Moreover, the operation switch group 22 is composed of a touch panel integrally formed with a surface of the output unit 24 that will be described later, and/or mechanical key switches installed in the surroundings of the output unit 24 together with other parts. The touch panel and the output unit 24 are layered to be combined with each other having the touch detection method of a pressure sensing type, an electromagnetic induction type, an electrostatic capacity type, or combination of those types.

The external memory 23 has the connection with the control unit 10 for sending and receiving data to and from the control unit 10, and thus stores the physical condition data and the like that is received by the control unit 10 from the physical condition measurement instrument 7 through the electric power line 5.

The output unit 24 is a color image display device that has a sound output unit, and the output unit 24 is connected with the control unit 10 in a condition that allows an output of the processing result performed in the control unit 10 as an image and/or a voice. More practically, the output unit 24 may be a liquid crystal display, an organic EL display, a CRT, or other device capable of outputting image/sound.

The remote control sensor 25 receives information such as a destination input from a remote controller 61 that serves as a remote control terminal, and sends the received information to the control unit 10.

In the above-mentioned navigation apparatus 4, the control unit 10 calculates the position, the travel direction, and the speed etc. of the vehicle 1 on the basis of the signal output from the position detector 15, and displays the map in the vicinity of the present location of the vehicle 1 that is read through the map data input unit 21 on the output unit 24 by executing certain processing. In this case, various methods are known as to request the present location on the basis of the signal from the GPS receiver 14 such as the single point positioning method or the relative positioning method, and both of which are acceptable.

Further, the control unit 10 executes other processing such as a route calculation for calculating an optimum route to the destination from the present location based on the destination set according to the operation of the operation switch group 22 and the remote controller 61 as well as the map data stored in the map data input unit 21, a route guidance for guiding the calculated route by displaying the route on the output unit 24.

The optimum route is set by using a technique such as a well-known Dijkstra method or the like.

Further, the navigation apparatus 4 becomes communicable with an external network 65 when the control unit 10 is connected with a cellular phone 35. As a result, the navigation apparatus 4 becomes capable of connecting to the Internet, and to a special information center.

The in-vehicle LAN 31 in the vehicle 1 is the communication network between the in-vehicle equipments in the vehicle 1. The LAN 31 has a connection to the above-mentioned plug 2a through a modem that is not show in the figure, and to the control unit 10 in a data communicable condition.

Further, the vehicle 1 has an accelerator opening sensor 51, a brake sensor 52, a vehicle speed sensor 53, and an acceleration/deceleration sensor 54. The accelerator opening sensor 51 is a sensor that detects opening of the accelerator, or the position of the accelerator, when the vehicle 1 is traveling. The brake sensor 52 is a sensor that detects the brake operation when the vehicle 1 is traveling. The vehicle speed sensor 53 is a sensor that detects the vehicle speed when the vehicle 1 is traveling. The acceleration/deceleration sensor 54 is a sensor that detects the acceleration and deceleration of the vehicle when the vehicle is traveling. The detection results of these sensors 51-54 are transmitted to the control unit 10.

The navigation apparatus 4 disposed in the vehicle 1 receives, by using the control unit 10, the physical condition data from the physical condition measurement instrument 7 through the in-vehicle LAN 31, and executes processing that determines the physical condition of the user 9 on the basis of the received physical condition data. Further, the control unit 10 determines whether the user 9 is performing a fuel-consumption-conscious driving operation based on travel condition detection results from each of the sensors 51-54. If the detection results indicate that the driving operation is not fuel-consumption-conscious, advice concerning the driving operation is output to the output unit 24 at a timing that considers the physical condition of the user 9.

(Explanation of Processing in the Control Unit)

Next, FIGS. 3 to 10 are used to describe the processing that is performed by the control unit 10.

Figure 3:
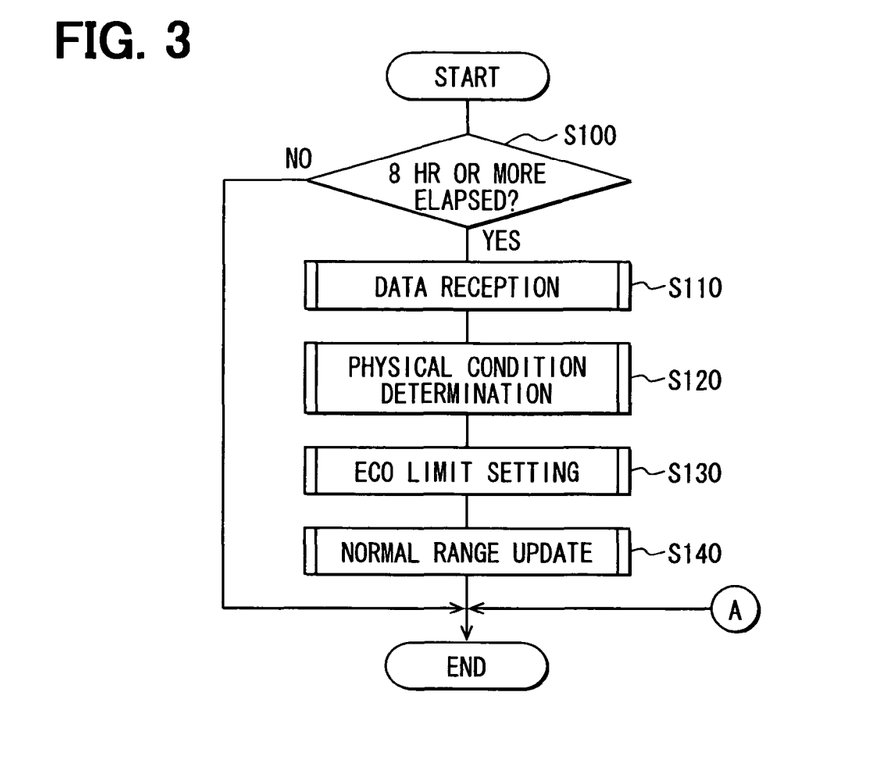
FIG. 3 is a flow chart of physical condition determination processing that is executed by a control unit of the navigation system in the embodiment.

FIG. 3 is a flow chart of processing that determines the quality of the physical condition of the user 9 for a certain day on the basis of the physical condition data. The processing is performed in the control unit 10 when the engine of the vehicle is not in operation and the vehicle is in a parked condition or in a stopping condition.

First, the control unit 10 determines whether eight hours have passed after setting a daily physical condition data and an eco limit described in detail in the following description (S100), and the process concludes itself without performing any step if it is determined that eight hours have not been reached ("NO" in S100).

On the other hand, if it is determined that eight hours have elapsed ("YES" in S100), processing that receives the physical condition data of the user 9 from the physical condition measurement instrument 7 is performed (S110). Details of step S110 are described later. Next, the physical condition determination processing that determines the quality of the physical condition of the user 9 is performed on the basis of the received physical condition data (S120). Details of step S120 are described later.

Next, processing of setting the eco limit is performed on the basis of the result of the quality determination regarding the physical condition of the user 9 (S130). The eco limit of a numerical value used for providing notice and warning described later is thus output. In step S130, processing that sets the eco limit is performed. Details of step S130 are described later.

Next, normality range update processing for setting/updating a normality range of the physical condition for a specific user is performed (S140). The normality range of the physical condition indicates that a criterion for determining that the quality of the physical condition of the user 9 in step S120. In step S140, the normality range of the physical condition is set by the processing. Details of step S140 are described later.

Figure 4:
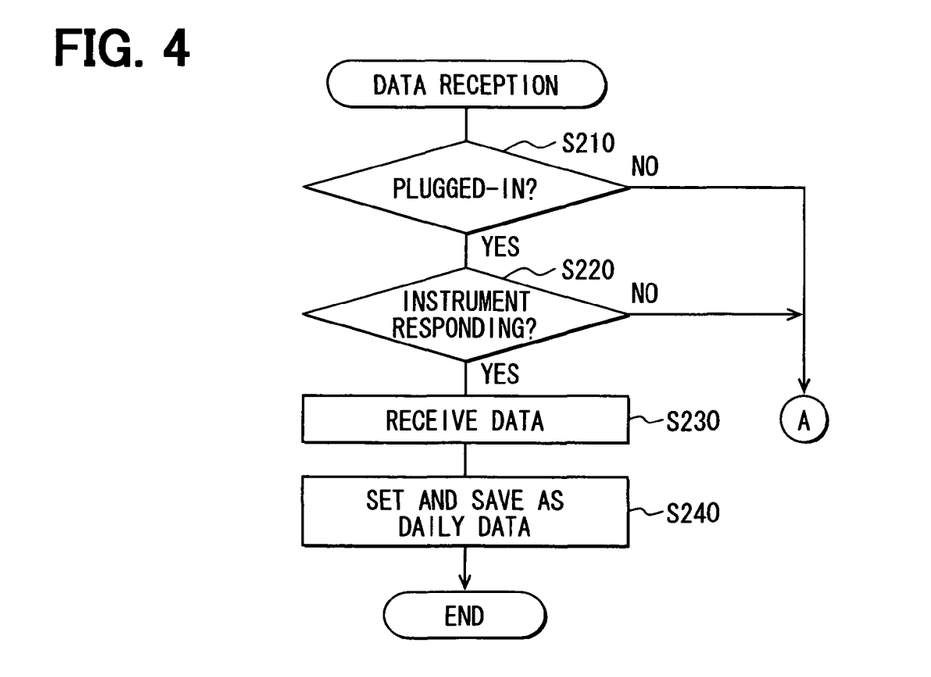
FIG. 4 is a flow chart of reception processing of the physical condition data in the embodiment.

FIG. 4 is a flow chart of the reception processing of the physical condition data of above-mentioned step S110. First, the control unit 10 concludes the processing shown in FIG. 3 without executing any step of the above-mentioned steps S110 to S140 when it is determined that the plug 2a is determined not to be inserted into the outlet 2b on the power line 5 ("NO" in S210).

On the other hand, if the plug 2a is determined to be inserted into the outlet 2b ("YES" in S210), then it is determined whether the physical condition measurement instrument 7 is responding (S220). If the instrument 7 is not responding ("NO" in S220), the processing concludes itself without executing any step from among steps S110 to S140.

On the other hand, if the instrument 7 is responding ("YES" in S220), the physical condition data is received from the physical condition measurement instrument 7 (S230), and the received physical condition data is set as the daily physical condition data, and is stored in external memory 23 by the control unit 10 (S240).

In this case, "the physical condition measurement instrument 7 is responding" indicates a situation that the physical condition measurement instrument 7 exists in the user's house 6 with the measurement of the physical condition of the user 9 for a sleeping time being completed. In other words, the situation can be described as that the physical condition measurement instrument 7 transmits a response signal to the control unit 10 in response to a response request signal from the control unit 10. When the response signal is received by the control unit 10, it is determined that the physical condition measurement instrument 7 is responding.

Further, as described above, multiple sets of the physical condition data are received and stored in the control unit 10 due to the measurement performed at every 1.5 hours by the instrument 7. In step S240, the control unit 10 calculates the average of the multiple sets of the data to be used as the daily data after receiving the data in step S230. In other words, the averaged body temperature, the averaged highest/lowest values of the blood pressure, and the averaged highest/lowest values of the pulse intervals are set as the daily physical condition data of the user 9 of a certain day.

Figure 5:
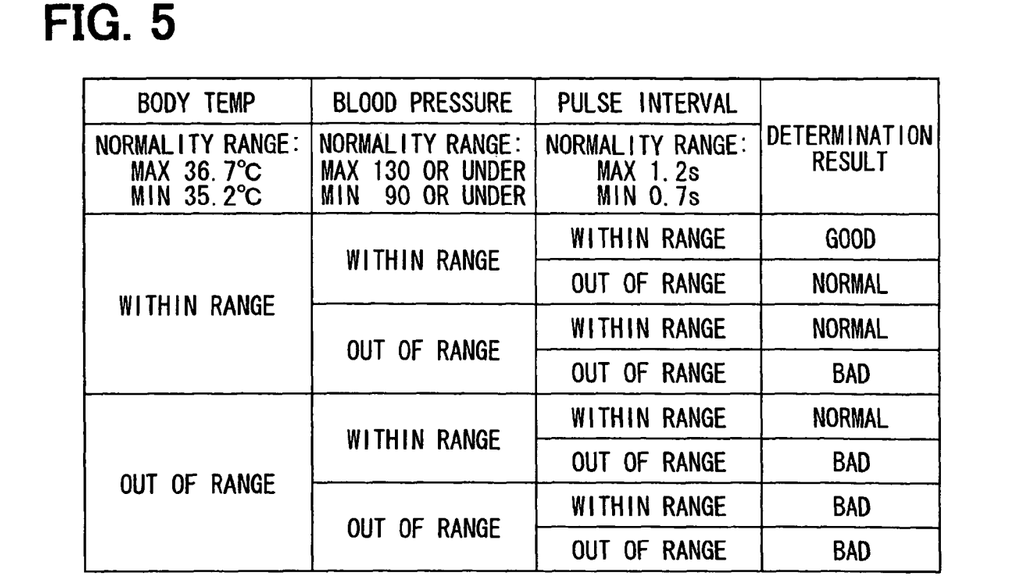
FIG. 5 is a diagram of reference data for determining the physical condition by the physical condition determination processing in the embodiment.

FIG. 5 is a data table that lists reference values for determining the physical condition by the control unit 10 in S120. The control unit 10 determines the physical condition of the user 9 such as Good/Normal/Bad based on the table in FIG. 5.

More practically, the control unit 10 determines whether the numerical value of each element in the daily physical condition data is within the normality range, and then determines that the user 9 is in "Good" condition when all elements of the physical condition data have the numerical value within the normality range. If one of the numerical value is determined as out of the normality range, the physical condition of the user 9 is determined as "Normal." Further, if two or more elements have the out-of-the-range value, the physical condition of the user 9 is determined as "Bad."

The normality range of the physical condition is a range of the numerical values regarding each element of the daily physical condition data that are stored in the external memory 23. Further, the initial setting of the range of the numerical values is set as a range of the numerical values that includes both of the maximum and minimum of the values of each element expected for normal, healthy people. More practically, the maximum/minimum values of the body temperature are set as 36.7/35.2 degrees: the maximum/minimum values of the blood pressure are set as 130 or under/90 or under: the maximum/minimum values of the pulse interval are set as 1.2 s/0.7 s. The numerical values of the normality range set as the initial setting are updated for the specific user 9 by the update processing of the normal physical condition range (S140) described later in detail.

Figure 6:
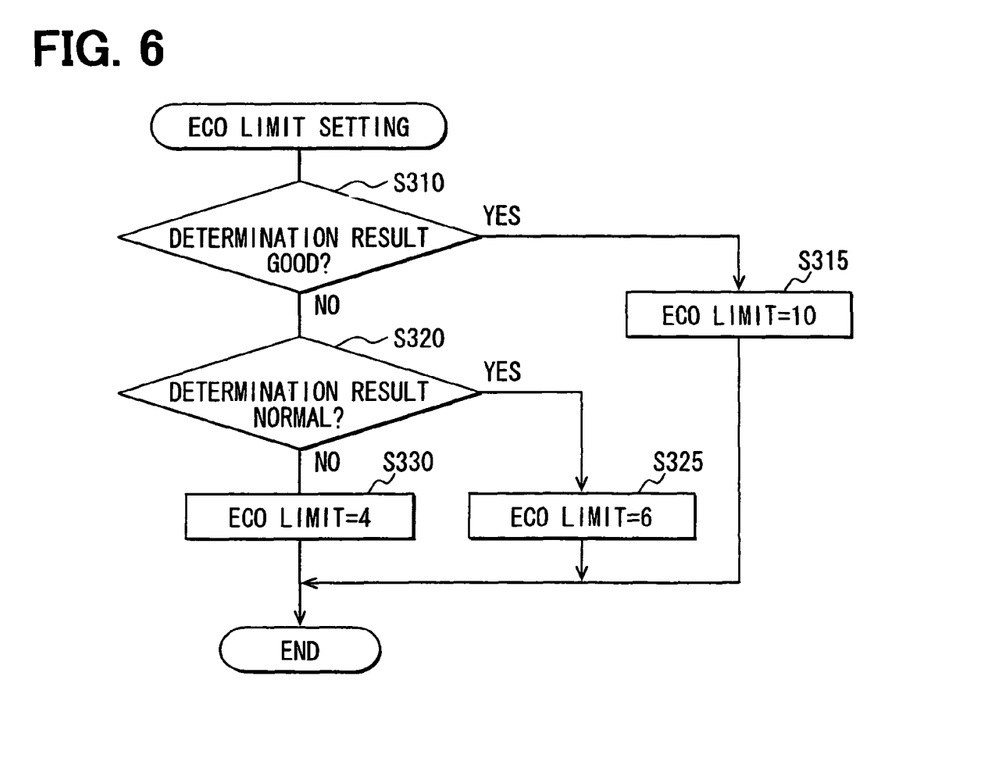
FIG. 6 is a flow chart of eco limit set processing in the embodiment.

FIG. 6 is a flow chart of the eco limit set processing performed in step S130. The control unit 10 determines first in S310 whether the physical condition determined in S120 is "Good," and sets the eco limit to "10" in S315 when it is determined as "Good" ("YES" in S310).

Next, when it is determined as not "Good" in S310 ("NO" in S310), the physical condition is further determined whether it is "Normal" or not in S320. If the condition is determined as "Normal" ("YES" in S320), the eco limit is set to "6" (S325).

Next, the eco limit is set to "4" in S330 when the physical condition is determined as not "Good" and not "Normal," that is, determined as "Bad" ("NO" in S320).

Figure 7:
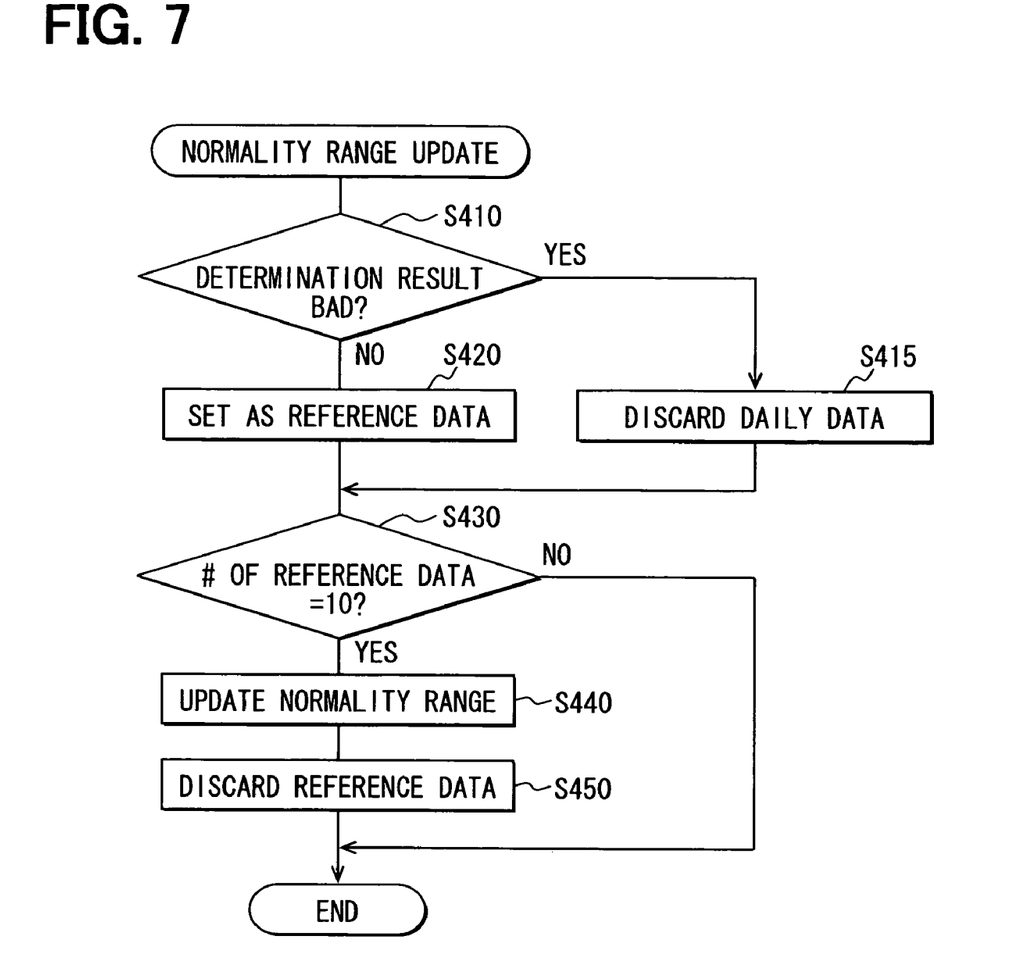
FIG. 7 is a flow chart of normality range update processing concerning the normality range of the physical condition in the embodiment.

FIG. 7 is a flow chart of normality range update processing regarding the physical condition in the above-mentioned step of S140. First, the daily physical condition data is deleted from the external memory 23 by the control unit 10 in S415 after determination whether the physical condition determination result in S120 is "Bad" ("YES" in S410).

On the other hand, if the determination result indicates that the physical condition is "Good" or "Normal" ("NO" in S410), the daily physical condition data is set as reference data to be stored in the external memory 23 in S420.

Next, in S430, whether the number of the reference data stored in the external memory 23 is equal to 10 or not is determined, and, if it is not equal to 10 ("NO" in S430), the update process concludes itself without performing any further step.

On the other hand, if the number of data is determined as equal to 10 in S430 ("YES" in S430), the normality range is updated by utilizing the reference data, and the updated value is stored as the normality range in the external memory 23 in S440. Then, after the update, all of the reference data used for the update is deleted from the memory 23. That is, all of the reference data is discarded in S450.

The computational method of update processing is specifically described with examples in the following. For instance, after 10 pieces of physical condition data are collected for the body temperature, the maximum value 36.5 degrees (Celsius) and the minimum value 35.8 degrees are going to be averaged with the maximum and minimum values stored in the table in FIG. 5 at the moment for updating the normality range. That is, for the body temperature normality range, the maximum value in the collected data '36.5' and the maximum value in the table '36.7' are taken to generate an updated average of '36.6' to be stored as a new maximum value of the body temperature normality range, if the updated processing is performed for the first time. As a result, the maximum value of 36.6 degrees and the minimum value of 35.5 degrees are stored as updated normality range values. Other elements such as the blood pressure and the pulse interval are processed in the same manner.

In the processing mentioned in FIGS. 3 to 7, the physical condition of the user 9 is determined based on the values set as the initial setting when the processing shown in FIG. 3 is performed for the first time. Thereafter, whenever, 10 pieces of physical condition data (i.e., physical condition data indicating either Good or Normal condition of the user 9) are collected, the normality range update processing shown in FIG. 7 is performed. By repeating the normality range update processing performed by the control unit 10, the values for defining the normality range of a specific user (i.e., the user 9) are going to have stable values, or, in other words, a user-specific value. Then, the user 9's condition is determined as Good/Normal/Bad by using the updated normality range values.

As mentioned above, the navigation apparatus 4 receives the physical condition data concerning the sleeping time of the user 9 in the user's house 6 that exists outside of the vehicle by processing shown in FIG. 4 performed by the control unit 10 through the power line communication. Further, by using the control unit 10, the navigation apparatus 4 executes the physical condition determination processing regarding the user 9 based on the table of the reference data shown in FIG. 5 and the physical condition data of the user 9.

In general, the user 9 is in a stable condition while he/she is sleeping. Therefore, the physical condition of the user 9 can be more appropriately determined based on the data of the sleeping time, in comparison to determination based on the data that is arbitrarily collected/measured regardless of the user's activity such as sleeping, working, walking or the like. That is, the data collected during the daytime while the user is not in the sleeping condition, for example, may not be reflecting the user's physical condition in an appropriate manner.

Further, by performing the processing shown in FIG. 7 in the control unit 10, values of the normality range are adjusted to the user specific values. That is, the user 9 specific normality range is stored as reference data. Therefore, the control unit 10 can more appropriately determine the physical condition of the user 9 by using the user specific normality range in comparison to determining the physical condition of the user by using a general/predetermined normality range.

Figure 8:
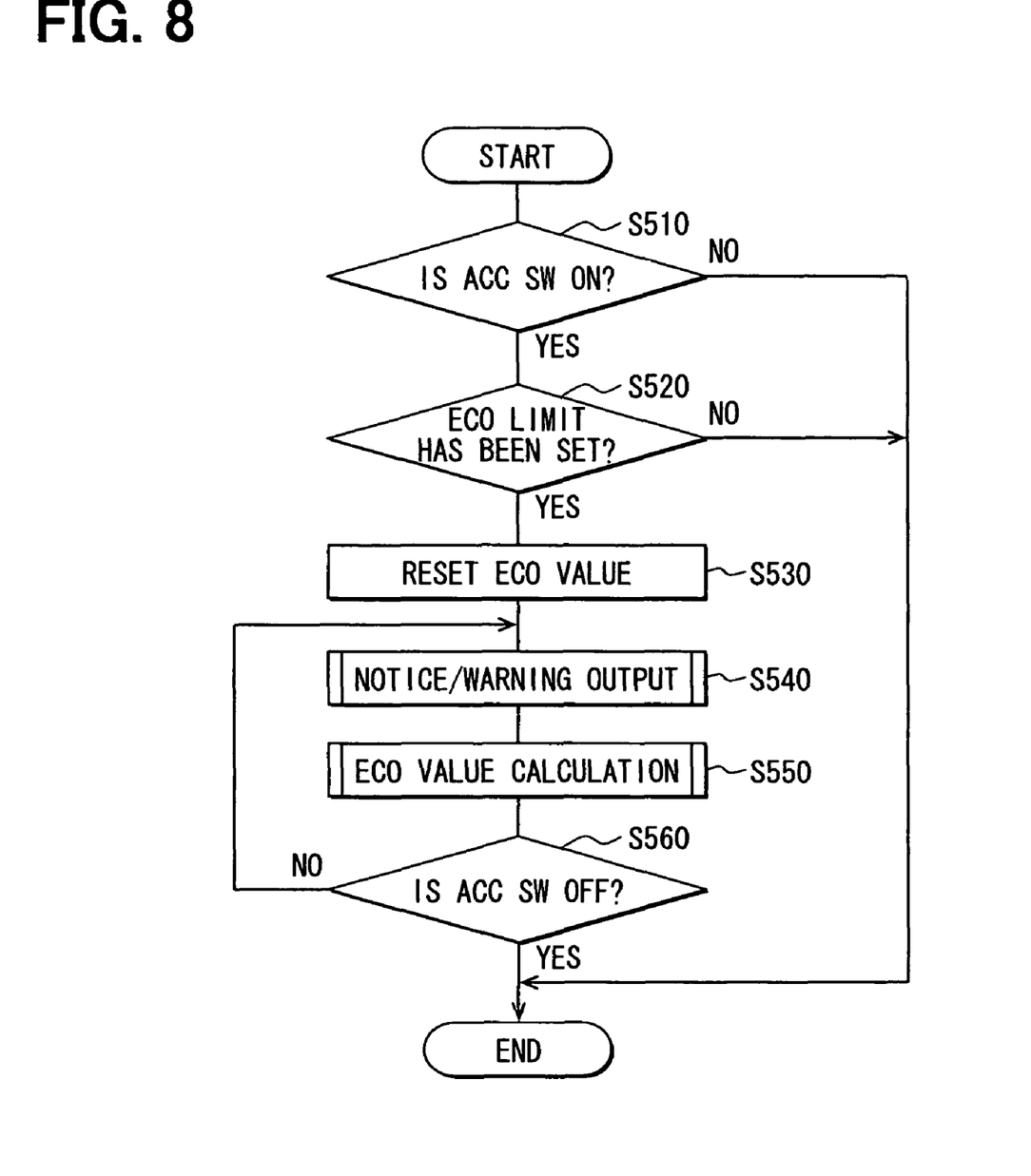
FIG. 8 is a flow chart of advice output processing for outputting an advice concerning the driving operation that is executed by the control unit of the navigation apparatus in the embodiment.

Next, processing that outputs advice concerning the driving operation according to the physical condition of the user 9 determined in the above-mentioned manner is described. FIG. 8 is a flow chart of processing that outputs advice concerning the driving operation to the output unit 24 according to the physical condition of the user 9. This processing is performed, regardless of the vehicle's condition such as traveling, stopping or parking, whenever the plug 2*a* is not inserted in the outlet 2*b*.

First, the control unit 10 determines whether ACC switch is turned ON (S510). If the ACC switch is not turned ON ("NO" in S510), the processing is finished without performing any step. On the other hand, if it is determined that the ACC switch is being turned ON in step S510 ("YES" in S510), whether the eco limit has been set is determined in S520. If the eco limit has not been set ("NO" in S520), the processing is ended as it is. On the other hand, if the eco limit is determined to have been set ("YES" in S520), the eco limit is initialized to have the value of "0" (S530).

Next, the notice/warning output processing is performed (S540). The notice and/or warning are the notice and/or warning in a form of advice concerning the driving operation of the user 9. The processing in step S540 outputs the notice and/or warning to the output unit 24. Details of S540 are described later.

Next, the eco value calculation processing is performed (S550).

Eco values are numerical values used in S540, and processing that calculates the eco values is performed in step S550. Details of S550 are described later.

Next, it is determined whether the ACC switch is turned OFF (S560). If the ACC switch is determined as being turned OFF ("YES" in S560), the processing is finished without performing any step. On the other hand, if the ACC switch is determined as being turned ON in step S560 ("NO" in S560), the notice/warning output processing is performed in S540 together with the eco value calculation processing in S550. Thereafter, the processing in S540 to S550 is repeated until the ACC switch is determined as being turned OFF.

Figure 9:
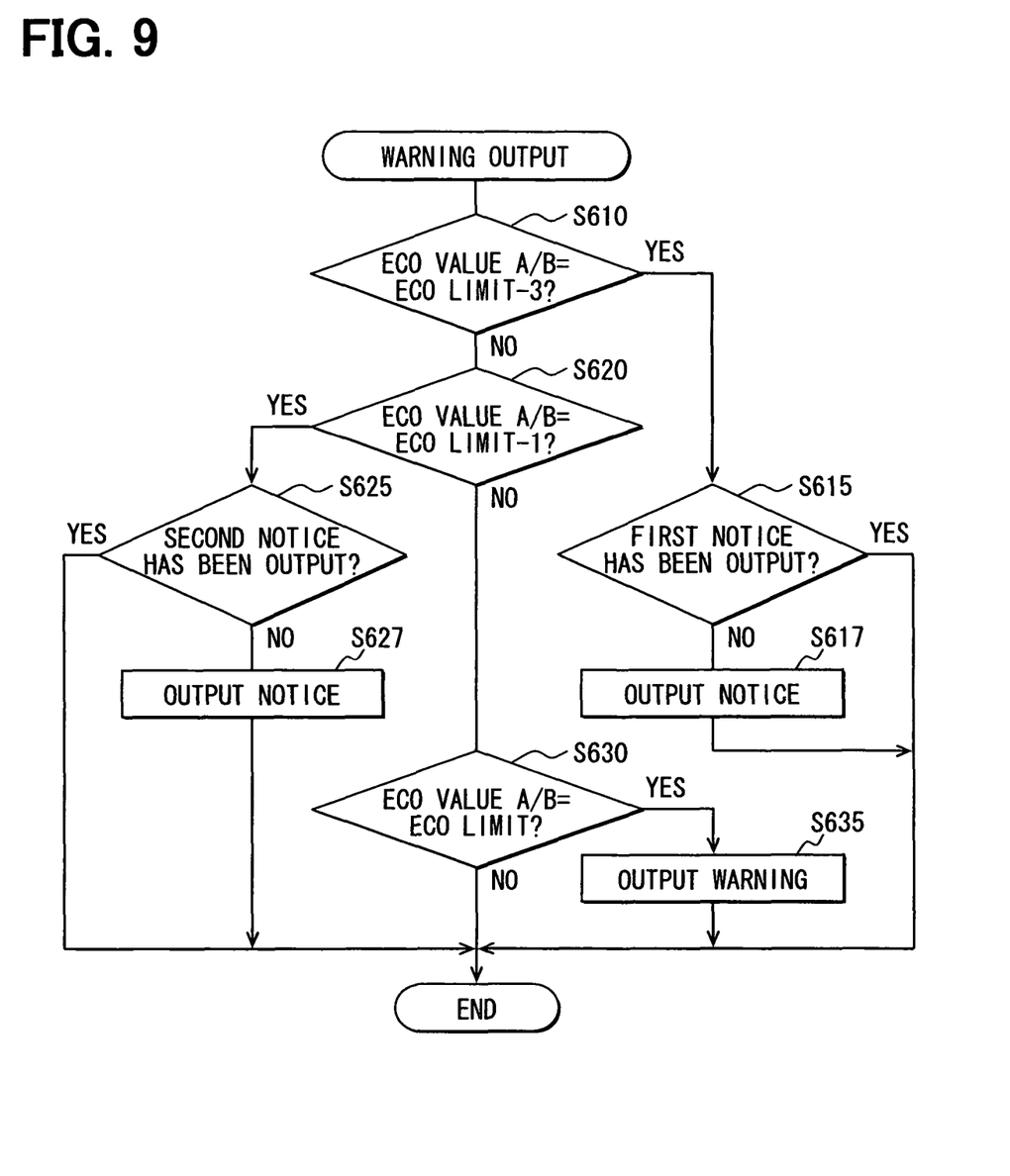
FIG. 9 is a flow chart of notice/warning output processing for outputting the notice and warning in the embodiment.

FIG. 9 is a flow chart of the output processing of the notice and warning in S540. The processing concerning the eco value A is described in the following, because the eco value B can be processed in the same manner as the eco value A.

First, the control unit 10 determines whether the eco value A is equal to the value of "Eco limit-3" (S610). If the eco value A is determined as equal to the value of "Eco limit-3" ("YES" in S610), it is determined whether the first notice corresponding to the eco value A has been output (S615). If the first notice is determined as not having been output ("NO" in S615), the notice corresponding to the eco value A is output (S617), and the processing is finished.

On the other hand, if the first notice is determined as having been output ("YES" in S615) even though the eco value A is determined equal to the value of "Eco limit-3" ("YES" in S610), the processing is finished without outputting the notice that corresponds to the eco value A.

Next, if the value A is different from the value of "Eco limit-3" ("NO" in S610), whether the eco value A is equal to the value of "Eco limit-1" is determined (S620). If the eco value A is determined as equal to the value of "Eco limit-1" ("YES" in S620), it is determined whether the second notice corresponding to the eco value A has been output (S625). If the second notice is determined as not having been output ("NO" in S625), the second notice corresponding to the eco value A is output (S627), and the processing is finished.

On the other hand, if the second notice is determined as having been output ("YES" in S625) even though the eco value A is determined as equal to the value of "Eco limit-1" ("YES" in S620), the processing is finished without outputting the notice that corresponds to the eco value A.

When the eco value A is determined as not equal to either of the "Eco limit-3" or "Eco limit-1" ("NO" in S610 and "NO" in S620), whether the eco value A is equal to the eco limit is determined in S630. If the eco value A is determined as equal to the eco limit ("YES" in S630), the warning corresponding to the eco value A is output (S635). On the other hand, if the eco value A is determined as not equal to the eco limits ("NO" in S630), the processing is finished without performing any further step.

The output of notice and warning mentioned above indicates that text message corresponding to the eco value in those steps is displayed on the screen of the output unit 24. The contents of notice and warning corresponding to each of the eco value in those steps are described later.

Figure 10:
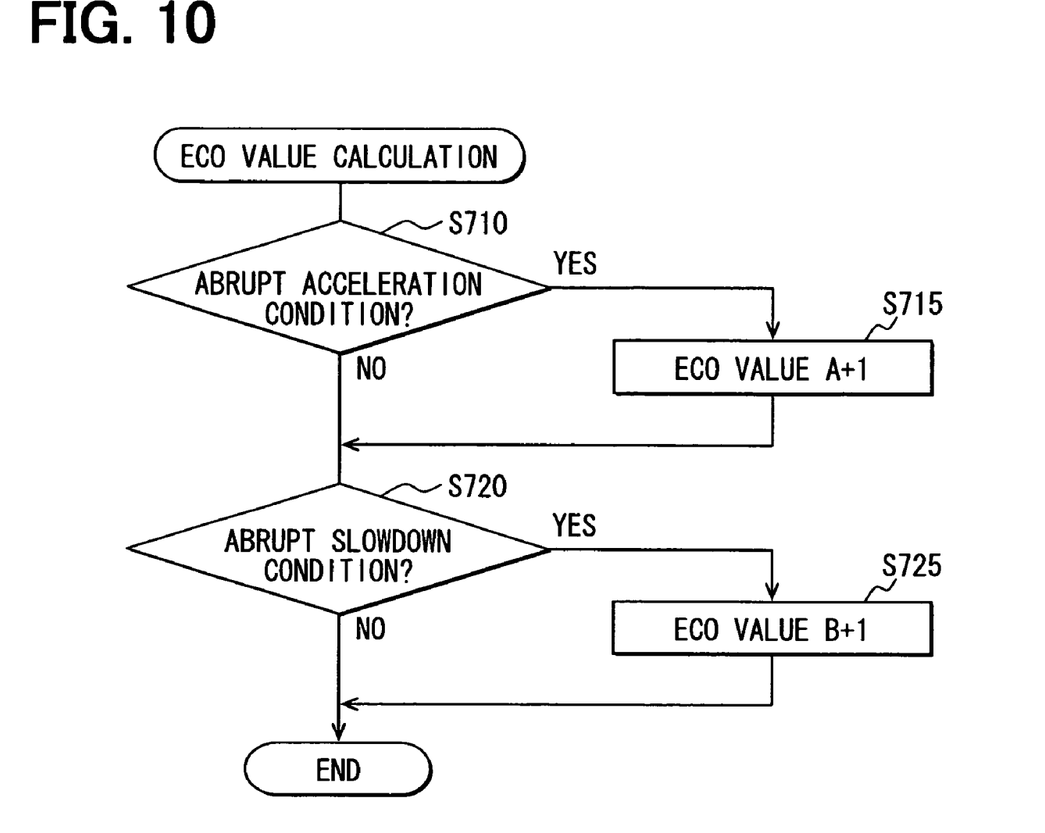
FIG. 10 is a flow chart of eco value calculation processing in the embodiment.

FIG. 10 is a flow chart of the eco value calculation processing in the above-mentioned step S550. First, the control unit 10 determines whether the vehicle 1 is in an abrupt acceleration condition on the basis of the detection results from each of the sensors 51 to 54 (S710). For instance, whether or not opening of the accelerator has increased equal to or more than 30% in a predetermined time is determined. If it is determined that the vehicle is in the abrupt acceleration condition ("YES" in S710), the eco value is increased by "1" (S715). On the other hand, if the vehicle is determined as not in the abrupt acceleration condition ("NO" in S710), the processing proceeds to the next step.

Next, the control unit 10 determines whether the vehicle 1 is in an abrupt deceleration condition (e.g., a steep/sudden braking) on the basis of the detection results from each of the sensors 51 to 54 (S720). For instance, whether or not the vehicle speed has decreased equal to or more than 40 km/h in a predetermined time is determined. If it is determined as the sudden braking condition ("YES" in S720), the eco value B is increased by "1" in S725, and the processing is finished. On the other hand, if it is determined that it is not the sudden braking condition ("NO" in S720), the processing is finished without increasing the eco value B.

When the abrupt acceleration or the abrupt deceleration is detected based on the driving operation by the user 9, the control unit 10 determines that the user 9 is performing a driving operation that is not fuel-consumption-conscious.

Further, the contents of notice corresponding to the eco value A may be "Slowly step on the accelerator pedal," and the contents of notice corresponding to the eco value B may be "Slowly step on the brake pedal." Furthermore, the first notice and the second notice are having the same contents. In addition, the contents of warning corresponding to the eco value A may be "Danger !: No Steep Acceleration," and the contents of warning corresponding to the eco value B is "Danger!: No Sudden Braking."

A specific value of the eco limit is used to describe a case where the control unit 10 is executing the processing shown in FIG. 8. For instance, suppose that the control unit 10 has determined that the physical condition of the user 9 is Good by the processing shown in FIG. 3, and has set the eco limit to the value of "10".

In that case, when the user 9 gets up from the bed and the engine of the vehicle 1 is started, the eco values A and B are both set to "0" ("YES" in S510, to "YES" in S520, to S530). Then, while the vehicle 1 is traveling, neither of the notice nor the warning are output to the output unit 24 of the navigation apparatus 4 as long as the user 9 performs the fuel-consumption-conscious driving operation driving operation (S540, to S550, to "NO" in S560).

If the user 9 performs the driving operation of, for example, the abrupt braking, the numerical value of the eco value B increases by "1" ("YES" in S720, to S725). Thereafter, the numerical value of the eco value B becomes "7" if the user 9 performs such driving operation seven times in total, and the first notice "Slowly step on the accelerator pedal" is output to the output unit 24 ("YES" in S610, to "NO" in S615, to S617).

In addition, the numerical value of the eco value B becomes "9" if the user 9 performs such driving operation nine times in total, and the second notice is output to the output unit 24 ("YES" in S620, to "NO" in S625, to S627). Then, the numerical value of the eco value B becomes "10" if the user 9 performs such driving operation ten times in total, and the warning "Danger !: No Sudden Braking" is output to the output unit 24 ("YES" in S630, to S635).

Thereafter, if the ACC switch of the vehicle 1 is turned OFF first to take a rest ("YES" in S560) and, in no time, the driving operation of the vehicle is resumed, the eco values A and B are both reset to "0" ("YES" in S510, to "YES" in S520, to S530). On the other hand, because the eco limit is determined according to the physical condition of the user 9 on a particular day, the value of the eco limit stays at "10" for performing the processing in the above-described manner.

The navigation apparatus 4, using the driving operation support scheme described in the present embodiment, outputs the notice and the warning concerning the improvement of the fuel consumption rate in an appropriate manner, according to the physical condition of the user 9 by performing the processing shown in FIG. 8, while the user 9 is driving the vehicle 1. The user 9 therefore can obtain an advice at an appropriate timing according to the user's physical condition that takes into the account the user's condition at an outside of the vehicle. Further, when the user 9 performs the driving operation according to the advice, the fuel consumption rate is improved, thereby contributing to solve the environmental problems.

In particular, when the user's condition is determined as Bad by the control unit 10, the eco limit is set to "4" by the control unit 10, and the first notice is output at once after determining that the non fuel-consumption-conscious driving operation is performed for the first time. In other words, the output frequency of the notice and warning is increased for the same number of times of the non fuel-consumption-conscious driving operation, in comparison to the case where the eco limit is set to "10" according to Good physical condition of the user 9.

According to the notice output scheme described above, the driving support system can call attention of the user 9 more frequently by increasing the output frequency of the notice and the warning even when the user 9 having the Bad physical condition is in an attention dispersed condition. Further, the output frequency of the notice and the warning will not be increased without considering the physical condition of the user 9, thereby not causing inconvenience due to the too-frequent notice/warning output for the user 9 who is in Good physical condition.

Other Embodiments

Although the present disclosure has been fully described in connection with preferred embodiment thereof with reference to the accompanying drawings, it is to be noted that various changes and modifications will become apparent to those skilled in the art.

For example, following changes and/or modifications can be possible.

The physical condition of the user may be determined not only by using the measurement of the body temperature, the blood pressure, and the pulse intervals of the user's sleeping time, as in the above-mentioned embodiment, but also be determined by using the measurement of, for example, the body temperature, the blood pressure, and the rhythm of change of the pulse intervals while the user is sleeping, or, the transition interval between REM sleep and Non-REM sleep, or the perspiration. That is, Good/Normal/Bad condition may be determined based on the measurement of the indicator other than the measurement of the body temperature or the like.

The user's body temperature is measured as the maximum value and the minimum value while he/she is sleeping in the above embodiment for determining the physical condition. However, the measurement may be processed in a different manner. That is, the deviation of multiple measurement values may be used to determine the user's condition. More practically, the smaller the deviation from a preset reference value, the physical condition determined as better, for example. Alternatively, if the number of the sampled data is large enough, the deviation may be calculated from those samples.

The normality range of the physical condition is updated when 10 pieces of the condition data are collected in the above embodiment. However, the update process may be performed when, for example, a predetermined time has elapsed after the last update. Alternatively, the user may determine the update timing.

The eco limit is set to a predetermined value according to the user's physical condition in the above-mentioned embodiment. However, the user may set the eco limit to a certain value. In this manner, the eco limit may be varied to the user-selected Good/Normal/Bad values according to the determination of the physical condition by the driving support system.

The output of the notice and the warning may take different forms that have been described as an output of the text message on the screen of the output device according to the eco value. That is, for example, the notice and the warning may be output as a sound message, or as a combination of the sound message and the text message on the screen.

The output of the notice and the warning may take different forms that have been described as an output from the navigation apparatus in the above embodiment. That is, for example, a dedicated output device of the driving support system may be disposed around the driver's seat for outputting the notice and the warning.

The travel condition of the vehicle may be determined not only by the detection result of the accelerator opening sensor, the brake sensor, the vehicle speed sensor, and acceleration/deceleration sensor in the above embodiment, but also by the detection result of the other/alternative sensors.

That is, all or part of the above sensors may be replaced with other sensors, as long as the travel condition can be determined in an appropriate manner. Further, additional sensors on the vehicle may be employed for the determination. That is, for example, the gyroscope in the navigation apparatus may be used for determining the travel condition.

The fuel-consumption-conscious driving operation may be determined based on the criterion that is different from the one used in the above embodiment. That is, any driving operation other than the abrupt acceleration/deceleration may trigger the notice and the warning output when the operation is considered as non-fuel-consumption-conscious. Further, an unsafe driving operation may also be notified and warned.

The unsafe driving operation may include, for example, according to the determination by the control unit, an abrupt lane change in a high speed, an abrupt U-turn in a high speed, or the like.

The physical condition of the user may be determined based on, for example, an additional condition other than the physical condition data of the user. That is, for example, the humidity and the temperature of the room where the user is sleeping may be taken into consideration for determining the physical condition of the user. More practically, whether the temperature/humidity is in a comfortable range may be determined based on the measurements of the temperature/humidity by the sensors in the air-conditioner in the user's room while the user is sleeping.

In this manner, the user's condition may be more appropriately determined based not only on the physical condition of the user collected by the instrument, but also on the environmental condition of the user's sleeping place.

Such changes, modifications, and summarized scheme are to be understood as being within the scope of the present disclosure as defined by appended claims.

What is claimed is:

1. A driving support system for supporting a user who is driving a vehicle, the system comprising:
   a physical condition measuring unit for measuring a physical condition of the user and for generating a condition data at an outside of a vehicle; and
   an information processor disposed on the vehicle for (a) receiving the condition data from the physical condition measuring unit through a power line that connects a battery in the vehicle and a power supply unit outside the vehicle for charging the battery, and for (b) providing an advice for driving operation at a timing that takes into consideration the physical condition of the user estimated from the condition data after (c) examining if the user is performing a fuel-consumption-conscious driving operation and (d) determining that the user is not performing the fuel-consumption-conscious driving operation (e) based on a vehicle condition reflecting driving operation of the user derived from sensors in the vehicle when the user is driving the vehicle.

2. The driving support system of claim 1, wherein
the information processor increases a frequency of advice outputs for the driving operation when the processor determines that the physical condition of the user is in a bad condition, in comparison to an output frequency when the user is determined to be physically in a good condition.

3. The driving support system of claim 1, wherein
the physical condition measuring unit measures at least one of user temperature during his/her sleep, user blood pressure, and user pulse interval.

4. The driving support system of claim 1, wherein
the sensors detect at least one of accelerator position, deceleration at a time of braking, degree of acceleration/deceleration and vehicle speed.

5. The driving support system of claim 1, wherein
the information processor outputs the advice for driving operation in at least one of a vocal manner and a visual manner.

\* \* \* \* \*